US011382772B2

(12) United States Patent
Bravo Castillo et al.

(10) Patent No.: US 11,382,772 B2
(45) Date of Patent: Jul. 12, 2022

(54) FINGER PROSTHESIS WITH ADJUSTABLE BIOLOGICAL ACTIVATION

(71) Applicant: PRO/BIONICS S.A. DE C.V., Estado de México (MX)

(72) Inventors: Luis Armando Bravo Castillo, Estado de México (MX); Magno Alcantara Talavera, Tlalnepantla de Baz (MX)

(73) Assignee: PRO/BIONICS S.A. DE C.V., Estado de Mexico (MX)

( * ) Notice: Subject to any disclaimer, the term of this patent is extended or adjusted under 35 U.S.C. 154(b) by 0 days.

(21) Appl. No.: 17/311,270

(22) PCT Filed: Jul. 4, 2019

(86) PCT No.: PCT/MX2019/050016
§ 371 (c)(1),
(2) Date: Jun. 4, 2021

(87) PCT Pub. No.: WO2020/251344
PCT Pub. Date: Dec. 17, 2020

(65) Prior Publication Data
US 2021/0353438 A1    Nov. 18, 2021

(30) Foreign Application Priority Data

Jun. 14, 2019  (MX) .................... MX/a/2019/007093

(51) Int. Cl.
*A61F 2/78*    (2006.01)
*A61F 2/58*    (2006.01)
(Continued)

(52) U.S. Cl.
CPC ................ *A61F 2/586* (2013.01); *A61F 2/78* (2013.01); *B25J 15/08* (2013.01); *A61F 2002/5007* (2013.01); *A61F 2002/5038* (2013.01)

(58) Field of Classification Search
CPC .... A61F 2/54; A61F 2/58; A61F 2/586; A61F 2/78; A61F 2002/5007; A61F 2002/5038; B25J 15/08
See application file for complete search history.

(56) References Cited

U.S. PATENT DOCUMENTS 1,929,926 A   10/1933  Laherty
2,867,819 A    1/1959  George
(Continued)

FOREIGN PATENT DOCUMENTS

CN   202235782 U   5/2012
CZ       25369 U1   5/2013
(Continued)

*Primary Examiner* — Bruce E Snow
(74) *Attorney, Agent, or Firm* — Berenato & White, LLC

(57) ABSTRACT

Prosthesis for at least one cut-off finger resulting in a stump at the height of the proximal, middle and/or distal phalange, or in a finger with missing stump. The prosthesis from a modular hinged mechanism allowing for a self-return flexion movement and the activation of said mechanism from at least one force applied to any point of a plane on said mechanism. A prosthesis for a hand with missing stumps is also provided from the wrist movement providing a range of operation greater than the art, wherein said flexion is activated from an extension movement of the wrist.

18 Claims, 7 Drawing Sheets

(51) Int. Cl.
*B25J 15/08* (2006.01)
*A61F 2/50* (2006.01)

(56) References Cited

U.S. PATENT DOCUMENTS

| | | | |
|---|---|---|---|
| 5,941,914 | A | 8/1999 | Jacobsen et al. |
| 6,908,489 | B2 | 6/2005 | Didrick |
| 6,913,627 | B2 | 7/2005 | Matsuda |
| 7,222,904 | B2 | 5/2007 | Matsuda |
| 7,481,782 | B2* | 1/2009 | Scott .................. A61F 2/72 601/40 |
| 8,021,435 | B2 | 9/2011 | Bravo Castillo |
| 9,629,731 | B2 | 4/2017 | Thompson, Jr. et al. |
| 10,842,652 | B2* | 11/2020 | Thompson, Jr. .......... A61F 2/78 |
| 2005/0043822 | A1* | 2/2005 | Didrick ............... A61F 2/586 623/64 |
| 2006/0212129 | A1* | 9/2006 | Lake .................. A61F 2/70 623/64 |
| 2011/0017008 | A1 | 1/2011 | Kanayama |
| 2016/0135967 | A1 | 5/2016 | Moyer et al. |
| 2020/0222209 | A1* | 7/2020 | Thompson, Jr. ........ A61F 2/586 |
| 2021/0022888 | A1* | 1/2021 | Garcia ............... A61F 2/5046 |
| 2021/0038409 | A1* | 2/2021 | Thompson, Jr. ........ A61F 2/586 |
| 2021/0052399 | A1* | 2/2021 | Cioncoloni ............ B25J 13/081 |

FOREIGN PATENT DOCUMENTS

| | | |
|---|---|---|
| DE | 327415 C | 10/1920 |
| JP | H05161667 A | 6/1993 |
| MX | 339274 B | 5/2016 |
| MX | 2015016647 A | 6/2017 |

* cited by examiner

FINGER PROSTHESIS WITH ADJUSTABLE BIOLOGICAL ACTIVATION

CROSS-REFERENCE TO RELATED APPLICATIONS AND CLAIM TO PRIORITY

This application is a national stage application of International Application No. PCT/MX2019/050016 filed Jul. 4, 2019, which claims priority to Mexican Patent Application No. MX/a/2019/007093 filed Jun. 14, 2019, the disclosures of which are incorporated herein by reference and to which priority is claimed.

FIELD OF THE INVENTION

The present invention generally relates to the field of mechanics and, more particularly, to the field of mechanical finger prostheses having a flexion and/or extension movement capability with fixed and/or adjustable biological activation, wherein said prostheses apply to those who have lost at least one distal, middle and/or proximal phalange, regardless of the amputation or cutting height.

BACKGROUND OF THE INVENTION

With the exception of the thumb, which has a greater movement capability, the functionality of the fingers of a hand depends mainly on its flexion and extension movements. However, it has been found that the flexion movement is most used, since it is with this movement that human is capable of gripping objects and carrying out various tasks.

When a finger amputation or cutting-off occurs, the use of prostheses is common to: hide or disguise the cut-off limb in an attempt to mimic the extension and/or flexion and/or both movements of the fingers. Similarly, the attempts to produce generic solutions in prostheses are not quite applicable, since the level of amputation or cutting-off usually varies from one case to another, turning each case into a particular solution. In this sense, it has been found in the art that a prosthesis of a cut off finger having, for instance, a proximal and/or middle phalange has a different design as compared with a prosthesis for a finger with missing stumps (because the amputation or cutting-off was made at a level beginning in the proximal phalange), since the scenario changes where there are residuals of at least one biological finger in the hand.

For example, the design of a finger prosthesis changes significantly when the affected part still has at least one proximal phalange, or proximal and middle phalanges, since said stumps have the capacity to perform a flexion and extension movement at the individual's discretion, and this can be used in the prosthesis design, as described in the Mexican Patent Application MX/a/2015/016647, which claims a finger prosthesis from a chain of links connected by joints and hinged pivots; however, the design depends entirely on the flexion and extension movements of the stump to which the prosthesis is applied.

In this sense the finger prostheses found in the art are designed so that each stump operates independently, without regard to the type of residual biological configuration to which said prostheses are applied. In this sense, the residual biological configuration of the affected limb relates to all biological elements that still remain in the cut off hand, i.e. after the accidental amputation or cutting-off, wherein these elements include the residual physiological capabilities. This is generally owing to the fact that accidents occurring in the industry encompass not only a single finger being cut off at a certain height, but also, depending on the activity that had led to the accident, a plurality of cut off fingers, thus resulting in a number of stumps being cut off at a different phalange level of one finger with respect to another adjacent finger, since fingers do not have a perfect alignment. Therefore, this is why every prosthesis design is virtually particular for each case.

Furthermore, it is important to describe the different scenarios in which a prosthesis can occur, for example, finger prostheses where the hand has at least one stump, wherein said prostheses are normally mechanical prostheses, since said stump performs the function of activation of the flexion and extension movement. However, a different scenario occurs in the case of a hand with missing stumps, wherein it has been found that there are electromechanical prostheses that use, for example, myoelectronics to generate the desired movement; however, the complexity of these prostheses makes the product too costly and, additionally, many of these prostheses provide limited grip strength capacity while also limiting the range of activities that the user of a prosthesis may perform. In this sense, the most important movements to be considered in a prosthesis are the grip movements, i.e. flexion, with different levels of strength. Therefore, there are electromechanical hand prostheses which provide sufficient grip strength, such as U.S. Pat. No. 8,021,435, which uses a worm gear mechanism with a clamp-type grip.

Furthermore, it has been found that an important aspect for users of prostheses, in addition to the functionality that a prosthesis may provide, is the appearance of said prosthesis. Thus, it is equally desirable for the prosthesis to have an attractive appearance which allows to disguise and/or avoid any attention that might embarrass the user. In this sense, it has been found that prostheses tending to emulate a biological hand or finger are the most accepted ones. Sometimes, the prosthesis appearance is more important than the prosthesis functionality itself.

The activation of a finger prosthesis relates to the biological, electrical, mechanical, and/or electromechanical mechanism necessary for said prosthesis to perform a movement, such as a flexion and/or extension movement, to a certain desired point, and to subsequently return to a default position. In this sense, it is common that said activation is made by the stump itself or, in the absence of a stump, it has been found that activation is made by using electromechanical and/or electronic means, such as myoelectric means.

For example, U.S. Pat. No. 6,913,627 B2 discloses a hand prosthesis using, for the fingers, a hinged mechanism with several links including pivots and rigid inter-joint connecting rods. However, the activation of the movement of this prosthesis occurs in the first joint, i.e. in the proximal end of the proximal phalange. This means that the leverage needed for the activations is minimum, such that the user needs to apply a great force with his/her stump to activate the prosthesis and even a greater force to hold an object and perform any task, and then an opposite or extension force to return the prosthesis to its default position. This causes fatigue and even pain in users, thereby resulting in a limitation in the operational capabilities of the prosthesis.

Furthermore, other means of finger prosthesis activation have been found, for example, U.S. Pat. No. 6,908,489 B2 or 9,629,731 B2, which are applied to a stump adjacent to a complete biological finger, wherein said complete biological finger performs the activation by a ring or similar device attached to the finger prosthesis, i.e. the adjacent biological finger performs the flexion and extension movement of the prosthesis to which it is rigidly attached. However, this technique uses a relatively high number of pieces which must be assembled to form a single prosthesis, thereby increasing its cost, and wherein said technique only allows the activation by using adjacent fingers.

U.S. Pat. No. 2,867,819 uses a simple hinged mechanism using a minimum number of pieces for its assembly, said hinged mechanism further including a simple spring so that, after a flexion movement, the finger prosthesis returns to a default position. However, this technique provides for a non-anthropomorphous movement by performing only the activation of a joint corresponding to the junction of the proximal phalange with the middle phalange.

In another line of thinking, in the case of fingers with missing stumps, hand or palm prostheses have been developed from mechanical arrangements that use wrist movement for activation thereof. However, said prostheses developments use the flexion movement of the wrist (when the wrist moves inwardly or towards the body) for the activation of a hook-type flexed mechanism. Thus, a combination of a wrist flexion with a hook-type flexed mechanism reduces the operational range of said prosthesis only to objects located near the user body, and it is therefore desirable to provide a technique that is capable, from mechanical means, of extending the operational range of prostheses for hands with missing stumps and activated by wrist movement, i.e. by biological activation.

Therefore, it is desirable to make use of the residual biological configuration of a cut off limb so that, from said residual biological configuration, a prosthesis can be designed which allows for the use of said configuration either in a modular or in a specific way, wherein it is important to reduce the number of pieces used. Additionally, it is desirable to prove a finger prosthesis which can be implanted in hands with fingers cut-off in different ways, i.e. which fit the residual biological conditions, where there is at least a cut-off finger having a stump, wherein the prosthesis is provided with the capacity to perform a flexion and/or extension movement, at the user's discretion, and making the most of said residual biological configuration.

Furthermore, it is desirable to design a prosthesis provided with biological activation for a hand with missing finger stumps, wherein in one particular embodiment the activation is performed with the wrist movement, i.e. the movement of the palm of the hand with respect to the forearm in at least one degree of freedom. In this sense, it is desirable that said prosthesis is able to be activated either by at least one flexion movement and/or by at least one extension movement and/or by the combination thereof.

On the other hand, it has been found that in a biological finger the rotation of the joints relative to each other does not have the same tempos or scopes, i.e. the rotation angle and the rotation velocity of a biological joint relative to other joint(s) are different, including the rotation angle and the rotation velocity of a biological finger relative to other finger(s). Therefore, it is desirable that the finger prosthesis can adjust its rotation scopes and velocities so as to result in a more anthropomorphous movement with respect to the art. In this sense, it is desirable to design a prosthesis that considers an anthropomorphous movement, i.e. that attempts to emulate the scopes and velocities at which biological phalanges at least partially rotate relative to one another.

Finally, it is desirable that the mechanisms used allows for the design of the phalanges or links of the prosthesis to be varied without affecting the functionality and appearance of the final prosthesis.

SUMMARY OF THE INVENTION

The present invention relates to systems, methods, devices and/or apparatuses related to mechanical finger or hand prostheses, wherein at least one finger has been amputated or cut off, either from its distal, middle and/or proximal phalange.

A common hand includes five fingers defined by links known as phalanges divided into proximal phalange (the one in contact with the body of the hand or palm), middle phalange and distal phalange. Wherein the first finger, the thumb, is comprised only by a proximal and a distal phalange. Phalanges are connected by joints allowing at least one degree of freedom, with a limited and common range of movement normally to provide for staggered flexion and/or extension movement (lateral rotation), in addition to one degree of freedom corresponding to the at least partially upward rotation in the first joint.

In one embodiment of the invention, it is provided a finger prosthesis manufactured from a kinematic chain defined by a plurality of links connected by at least a first simple joint between adjacent links and at least one solid elongated body i.e. rod, connecting two non-adjacent links by way of a second simple joint between: an end of said solid elongated body with the closest end of one of said two non-adjacent links, and the other end of said rigid elongated body with the closest end of the other of said two non-adjacent links.

In this sense, in one embodiment of the invention, a joint is defined as a generally circular cross section shaft which may or may not be a rotary shaft used to support rotary wheels, pulleys and/or similar elements. In this case, said elements are used to support two links providing at least one angular degree of freedom of one link relative to one another.

The rod hingedly connects non-adjacent links by pushing and/or pulling, thus causing the links to rotate relative to its joints, and wherein the location of each rod end, also called pivot, and the rod length may vary so as to provide for a different resulting pivot movement between the links, including accelerations and/or velocity variations at certain points of the movement. Thus, this mechanism with hinged pivots allows, when a first link representing a phalange is moved, that the other links are also moved accordingly by the rigid connection represented by the rod, and wherein said resulting movement has a direct relationship with the location of the joint and of its corresponding pivot. In this sense, in one embodiment of the invention, quadrants are defined for the location of the pivots with respect to the corresponding joint, such that when the pivot is located in a quadrant, an acceleration/deceleration of the resulting movement is achieved. Therefore, in one embodiment of the invention, the location of the pivots is performed in quadrants providing anthropomorphous accelerations/decelerations. Furthermore, in one particular embodiment, the pivot in each quadrant is situated in different locations, either near or far from the joint, so as to provide for movements whose component in X is greater or less with respect to the other component, and/or movements whose component in Y is greater or less with respect to another component.

In one embodiment of the invention, the pivots are situated in the same hemispheres or pair of quadrants with respect to the horizontal axis (X axis) and/or the vertical axis (Y axis). In one embodiment of the invention, the pivots are situated in different hemispheres or pair of quadrants with respect to said horizontal and/or vertical axis.

The finger prosthesis of the present invention is made by connecting links by means of joints, thereby defining a kinematic chain comprised by at least two links and wherein hinge rods are coupled to non-consecutive links. In one particular embodiment, each link having a preferably elongated shape, such that the joints are situated in each substantially distal end of said elongated shape. It will be apparent to a skilled in the art that the shape of the links may vary without affecting the subject matter of the present invention, and that said shape may be not only elongated, but it may also be a combination of different shapes, including a combination of biological shapes.

Furthermore, in one embodiment of the invention, each joint between links provides for at least one angular and/or displacement degree of freedom by means of a slider. In one particular embodiment, said at least one degree of freedom is an angular degree of freedom. In one particular embodiment, said at least one angular degree of freedom is a movement representing the flexion and/or extension, or an at least partially lateral rotation, of the finger. In one particular embodiment, between each pair of non-adjacent links is situated a pivot rod defined by a rigid elongated piece whose ends are coupled to a link at a pre-established distance from the joint or axis, such that a link A is connected in a pivot relationship via a pivot rod to a link C, crossing link B, wherein link A and link B are non-adjacent links, and link A and B having an articulated relationship, and link B and link C also having an articulated relationship. In one embodiment of the invention, the rod is a rigid rod. In one embodiment of the invention, the rod is a straight rod. In one embodiment of the invention, the rod has an undulated shape. In one embodiment of the invention, the rod is compression and/or extension elastic. In one embodiment of the invention, the rod has an end-to-end length that is substantially equal to the inter-joint distance of the links connected by said rod, i.e. the end-to-end length of the rod is substantially the same as the length of at least one crossing link. In one embodiment of the invention, the pivot rod is either greater or less than the inter-joint or inter-axis crossing distance in a range from 0-25%.

In one embodiment of the invention, a spring or system of springs causes the finger prosthesis of the present invention to automatically return to a default position when a force is no longer applied. In one particular embodiment of the invention, the spring is applied to generate the extension movement. In one particular embodiment, the default position may be adjusted via mechanical means known in the art, which at least partially adjust the link dimension either in X and/or in Z so that the prosthesis itself reaches a physical restraint. Thus, in one particular embodiment, a projection adjustable in height is coupled to the link via a screw-nut relationship, wherein said projection can be adjusted in height as the projection rotates in one direction or the other. In one particular embodiment, the spring system returning the mechanism to a default position is in the joints of the link corresponding to the proximal phalange, either at one end and/or at the other end thereof. In an alternative embodiment, the spring system is in the joints of the link corresponding to the middle phalange, either at one end and/or at the other end thereof.

Therefore, the finger prosthesis formed from the kinematic chain described herein is activated by at least one force that can be situated at any point of any link, wherein the leverage causing said force with respect to the links generates an at least partially lateral rotation. In one embodiment of the invention, at least one link or phalange includes mechanical means for ease of activation of the prosthesis. In one particular embodiment, said mechanical means are defined by at least one trigger comprised by a rod laterally extending from any point of any link outwardly in one and/or two directions. In one particular embodiment, the length of said rod varies according to the residual biological configuration of the user, such that said rod may have a length allowing the activation thereof by at least one finger and/or stump.

In this sense, in one embodiment of the invention, the mechanism of the present invention includes a configuration that allows activation by a flexion movement, and an elastic arrangement coupled to said mechanism and to a reference generates an extension movement to return the mechanism to a default position. In another embodiment of the invention, the mechanism of the present invention includes a configuration that allows activation by an extension movement, and an elastic arrangement coupled to said mechanism and to a reference generates a flexion movement to return the mechanism to a default position. It will be apparent to a skilled in the art that the reference to which said elastic arrangement is coupled may be or not any part of the user's body which remains fixed with respect to the mechanism, and that the selection and/or location of said reference may vary without affecting the subject matter of the present invention.

In this sense, it has been found that, in a default position of one embodiment of the mechanism of the prosthesis of the present invention, the initial location of the pivots will show a sinusoidal/cosinusoidal behavior after the application of an activation force triggering the desired flexion and/or extension movement. Thus, in one embodiment of the invention, said mechanism includes links whose design allows for adjustment of the location of the joints and/or the ends of the pivot rod. In one particular embodiment, the link design includes a plurality of receptacles or orifices in which the links can be separately coupled, keeping an articulated relationship of lateral rotation, either at least one trigger, at least one joint and/or at least one pivot rod end.

In one embodiment of the invention, each rod end is hingedly coupled to the respective link via a circular shape, i.e. the link includes a circular orifice or a circular orifice bearing, and the rod end is introduced into said orifice so as to allow said articulated relationship, i.e., said rod end is capable of working as an axis. In one particular embodiment, the link orifice has a slider-type elongated shape so as to allow for the rod end, in addition to rotating, to move along at least a Cartesian plane or component. It will be apparent to one skilled in the art that the slider-type elongated orifice providing for displacement of the pivot may vary in shape without affecting the subject matter of the present invention, wherein such elongation may be straight, curved and/or combinations thereof.

In an embodiment, the prosthesis of the present invention includes mechanical means coupled to the surface of any of the links so that said prosthesis may be activated by the flexion and/or extension of at least one biological finger and/or stump adjacent or not to the prosthesis. In this sense, it will be apparent to a skilled in the art that said mechanical means to perform said activation or triggers may vary without affecting the subject matter of the present invention, such that said means may include, but are not limited to: a protrusion, a coupled rod, an ergonomic-shape trigger, etc., wherein said coupling is made by means already known in the art. In one particular embodiment, the finger prosthesis includes a plurality of trigger receptacles or activation means so that at least two activation means may be coupled to said prosthesis and/or the location of said activation means may be adjustable.

Furthermore, in an embodiment, a spring is coupled to the mechanism of the present invention to ensure a mechanical self-return to a default position of the prosthesis after said prosthesis has been activated, i.e. after an activation force is ceased to be applied. In this sense, in one particular embodiment, the spring is coupled to perform the extension movement, and the activation is performed by applying a force that causes the flexion movement. In another particular embodiment, the spring is coupled to perform the flexion movement, and the activation is performed by applying a force that causes the extension movement.

In one embodiment of the invention, at least one joint has an elongated orifice allowing the rotation and the displacement in at least one Cartesian plane or component between adjacent links. It will be apparent to a person skilled in the art that the elongated orifice allowing the displacement of the joint may vary in shape and dimensions without affecting the subject matter of the present invention, wherein such elongation may be straight, curved and/or combinations thereof.

In one embodiment of the invention, the link is a rigid piece. In one particular embodiment, the link is a hollow piece. In a further particular embodiment, the link is a hollow piece at least partially allowing for accommodation of a stump.

In one embodiment of the invention, the pivot rod is a rigid solid body.

In one embodiment of the invention, at least one link includes flexible mechanical means to be adjustably coupled to a stump or biological part of a user. In one particular embodiment, said flexible mechanical means are defined by a belt or wristlet known in the art, which is adjustably secured to a stump or biological part of a user.

BRIEF DESCRIPTION OF THE DRAWINGS

Some of the measures and/or dimensions of the figures shown have been exaggerated for purposes of illustration.

DETAILED DESCRIPTION OF THE INVENTION

The following description is provided to enable those skilled in the art to make and use the embodiments, and said description is provided within the context of a particular application and the requirements thereof. Various modifications to the embodiments disclosed herein will become easily evident to those skilled in the art and the general principles defined herein may be applied to other embodiments and applications without departing from the spirit and scope of the present disclosure. Therefore, the present invention is not limited to the embodiments shown, but on the contrary, the present invention must conform to the widest scope consistent with the principles and characteristics disclosed herein.

In this document, the term kinematic chain relates to open kinematic chains, since several links are connected with each other, such that a relative motion between the links is possible, and an output motion controlled in response to an input motion or force is provided, and wherein the end links are not fixed. Furthermore, this description relates to a mechanism when a kinematic chain has at least one of its end links fixed relative to the other links, such that a same chain can produce several different mechanisms.

Figure 1A:
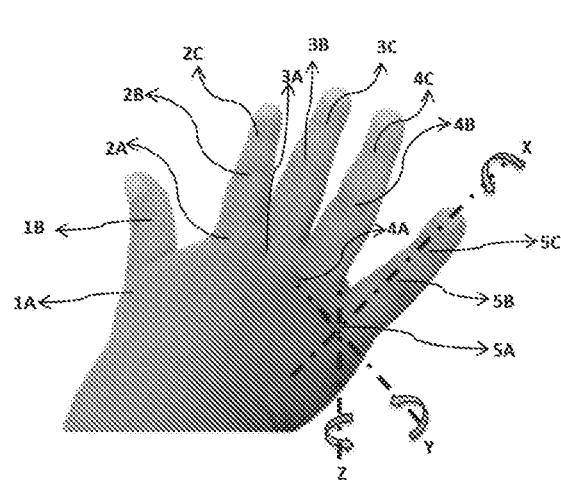
FIG. 1A shows a perspective view of a biological hand having all of its fingers, including the type of movement performed by said fingers, and depicting an analysis of the movement of the fifth finger.

FIG. 1A shows a perspective view of a hand with all of its biological fingers, wherein the parts of each finger and the movements of the fifth finger in its first joint are illustrated. Thus, each finger is shown from the first finger to the fifth finger, divided into its proximal, middle and distal phalanges. For instance, the second or index finger of the hand is divided into a proximal phalange connected to the hand by joint 2A, a middle phalange connected to the proximal phalange by joint 2B, and a distal phalange connected to the middle phalange by joint 2C. The same joints 3A, 3B, and 3C are provided in the third finger; joints 4A, 4B, and 4C are provided in the fourth finger; and joints 5A, 5B, and 5C are provided in the fifth finger. In this sense, joint 2A of the proximal phalange with the palm of the hand normally includes at least two degrees of freedom, at least partially. Thus, as shown by way of illustration in the fifth finger or little finger with respect to its joint 5A, an X axis or horizontal or longitudinal axis, a Y axis or lateral or transversal axis, and a Z axis or vertical axis are shown, such that the rotation or degree of freedom around the X axis is defined as the longitudinal rotation or roll, the rotation or degree of freedom around the Y axis is defined as the lateral rotation or pitch, and the rotation or degree of freedom around the Z axis is defined as the vertical rotation or yaw. In this sense, biological fingers normally include a partial vertical rotation and a partial lateral rotation in the joints corresponding to the proximal phalange with the palm of the hand; a partial lateral rotation in the joint connecting the proximal phalange with the middle phalange; and a partial lateral rotation in the joint connecting the distal phalange with the middle phalange. In this description, the joint movements from the proximal phalange to the distal phalange will be called first lateral rotation, second lateral rotation, and third lateral rotation, respectively.

Figure 1B:
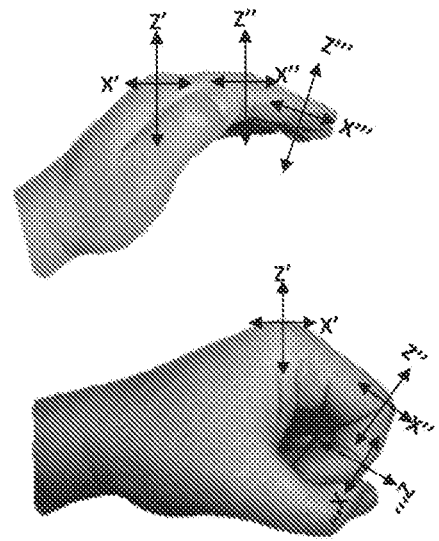
FIG. 1B shows a side view of the natural movement of a second biological finger, in a semi-extended position and in a flexed position, wherein said figure additionally shows planes with the Z axis (vertical axis) and the X axis (horizontal axis) on the joints corresponding to the Y axis or lateral axis.

FIG. 1B shows a side view of a biological hand in an extended position and in a flexed position, wherein the flexion movement of the second biological finger is analyzed. Furthermore, in a first position, the location and orientation of consecutive planes with vertical axis (Z axis) and horizontal axis (X or longitudinal axis) on each biological joint is shown. In this sense, according to the analysis provided herein, the rotation to be performed by a biological phalange with respect to another phalange will be a lateral rotation or a rotation around the Y axis, unless otherwise specified. Thus, it can be observed how the planes on each joint rotate and displace in a like manner relative to its original position. The horizontal axis of each plane is defined as a straight line crossing the joint with another adjacent front joint even after the movement has started, wherein the elements are started to be numbered from the part closest to a user's body or proximal end.

Figure 2A:
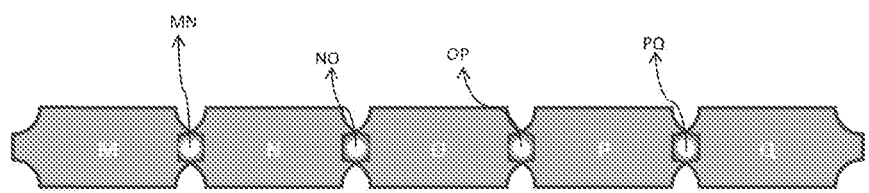
FIG. 2A shows a diagram of a kinematic chain with five links connected to each other by hinge means or joints providing at least one degree of freedom.

FIG. 2A shows a side view of a chain formed by a plurality of links M, N, O, P, Q hingedly connected by a simple joint or shaft providing an angular degree of freedom. In this sense, said joint is in direct contact with at least two links, i.e. each shaft crosses the body of two adjacent links M-Q, such that each link has a relative motion with respect to an adjacent link with which it has an articulated relationship.

Those skilled in the art will appreciate that an articulated relationship would be defined as the connection between at least two elements or bodies, wherein said connection further allows for at least one angular degree of freedom rotating around X, Y, and Z axes, and/or in one particular embodiment of the invention, wherein at least one lineal or displacement degree of freedom allowing the axis to be displaced along at least one Cartesian component is further included.

Figure 2B:
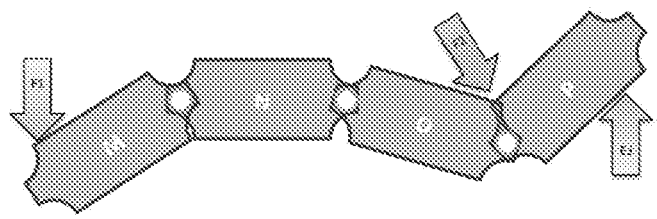
FIG. 2B shows the kinematic chain in FIG. 2A, wherein said chain has been subjected to a plurality of forces, wherein each link reacts and moves according to the force exerted on said link and/or according to the movement triggered by the other links.

FIG. 2B shows the behavior of the chain in FIG. 2A, wherein three forces F1-F3 have been applied in different directions and points on said chain, wherein it can be appreciated that each link is independently affected by each force according to the vector characteristics of said force, i.e. according to the magnitude, direction, sense, and point of application of the force.

Figure 2C:
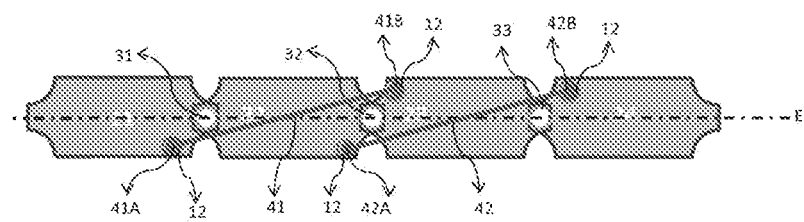
FIG. 2C shows the kinematic chain of the present invention, wherein rods are coupled between two non-consecutive crossing links, crossing, without at least partially touching, a third link to provide a pivot relationship between said two non-consecutive links and said third link.

FIG. 2C shows an embodiment of the mechanism of the present invention with links 21-24 in an aligned position defined by the straight line E crossing all the joints in a moment in which said joints are aligned, wherein pivot rods 41 and 42 have been coupled to pairs of pivot ends 41A, 41B, 42A, and 42B respectively coupled around each joint 31, 32, and 33. In this sense, it can be appreciated how each pivot rod is coupled to non-adjacent links. For instance, around joint 31 (which crosses links 21 and 22 providing rotation between them) is located pivot 41A, which only touches link 21. Similarly, around joint 32 (which crosses links 22 and 23 providing rotation between them) is located pivot 41B, which only touches link 23; and pivot 42A, which only touches link 22, and so on. Thus, since pivot rods 41 and 42 are rigid, these are pivotably coupled, such that each rod hingedly connects non-consecutive links in addition to the joint already present in the adjacent links. For example, rod 42 particularly connects link 22 with link 24 without having any direct contact with link 23. Furthermore, in one embodiment of the invention, the point of coupling of the pivot rod ends to the link is defined by a bearing 12. In one particular embodiment, the bearing 12 includes a self-alignment mechanism. Furthermore, in one particular embodiment, said bearing 12 has such a shape that, in addition to accommodating a shaft to allow for rotation, said bearing allows for a controlled displacement of said shaft; that is, in addition to the rotation, said bearing allows for an oscillating displacement of at least one pivot rod end.

Figure 2D:
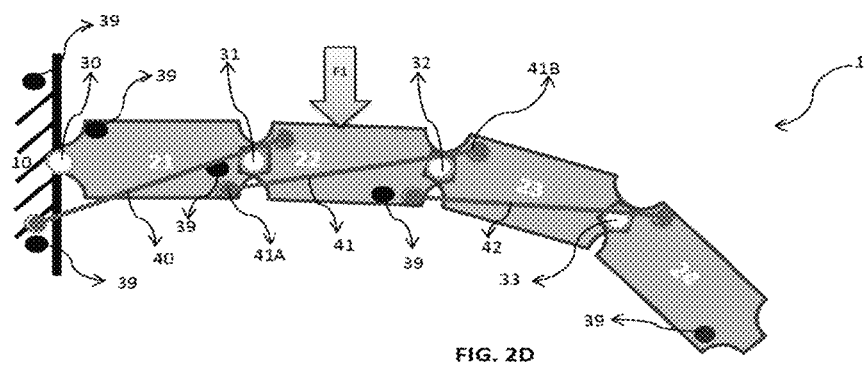
FIG. 2D shows the mechanism of the present invention, wherein an end link is fixed relative to the other links, and wherein a flexion force F1 is applied to one of the links, according to the movement of a biological finger.

Thus, FIG. 2D shows the behavior of mechanism 1 of an embodiment of the present invention when the first link is attached to a fixed or reference part 10 and when a force F1 is applied, wherein it can be appreciated that the links maintain an even behavior in a direction when adjacent links are connected by means of joints 30-33 and when non-adjacent links are connected by means of solid bodies such as the pivot rods 40-42. Furthermore, receptacles 39 of the pivot rod end can be appreciated, which, in one embodiment of the invention, are spaces available along the surface of at least one link to adjust the location from one point to another point of any pivot rod end. An adjustment in the distance and separation angle between one pivot point and a joint results in an adjustment in the resulting motion of any mechanism.

Figure 2E:
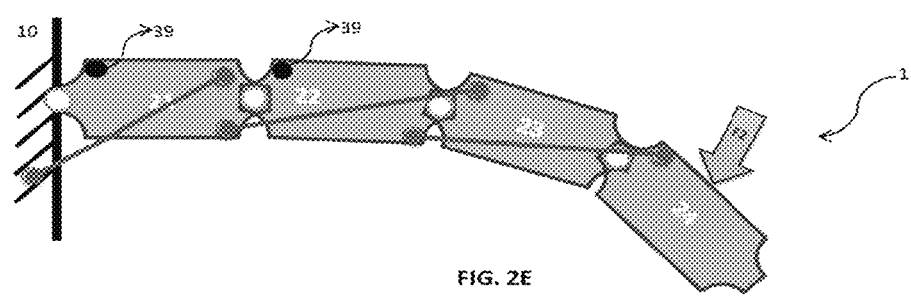
FIG. 2E shows the mechanism of the present invention, wherein an end link is fixed relative to the other links, and wherein a flexion force F2 different from force F1 is applied to another link, and wherein the same resulting triggered flexion movement is shown, regardless of the point of application of said flexion force F1 or F2.

FIG. 2E shows the mechanism 1 in FIG. 2D when a force F2 is applied, and wherein said force F2 is different from force F1. However, both forces, in at least one of its components, provide for a flexion movement in the mechanism, in this case, a triggered downward lateral rotation. In this sense, a person skilled in the art will appreciate that the applied force may be illustrated differently without affecting the subject matter of the present invention, and that said force may also be a shear force, a flexion force, a leverage, etc.

Figure 2F:
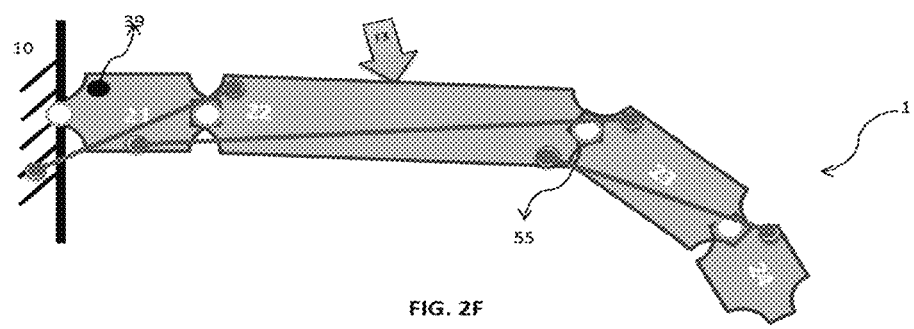
FIG. 2F shows the mechanism of the present invention, wherein the links are different from each other, and wherein a flexion force F3 different from force F1 and force F2 is applied to a different link, and wherein a similar resulting triggered flexion movement is shown, regardless of the point of application of said flexion force. Additionally, it can be observed that, when the shape of any of the links and/or the point of application of the rod pivots is modified, the flexion movement is also adjusted.

FIG. 2F shows an embodiment of mechanism 1 of the present invention, wherein the shape and dimensions of links 21-24 have been changed, and wherein said mechanism is flexed with the triggering of some links with other links by applying a force F3, wherein any of the components of said force provides the leverage needed to move the flexed mechanism. In this sense, those skilled in the art will appreciate that the shape of the links may vary without affecting the subject matter of the present invention, wherein said shape may be a regular, symmetrical, or asymmetrical shape, or wherein said shape may emulate real biological shapes such as the shape of a human finger, automated or futuristic shapes. Furthermore, those skilled in the art will appreciate that the shape and dimensions according to which links are manufactured may vary without affecting the subject matter of the present invention.

Figure 2G:
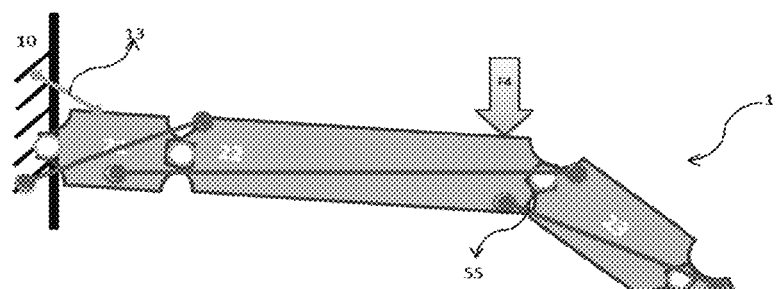
FIG. 2G shows the mechanism in FIG. 2F in two different positions, in a flexed position by the application of a force F4, and in a default position to which the mechanism returns via an extension force generating elastic means coupled to the mechanism and to a fixed or reference position.
Figure 2G:
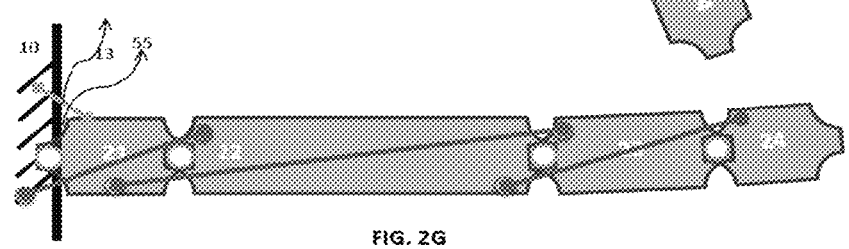

FIG. 2G shows the mechanism 1 in FIG. 2F in two different positions in separate moments. Thus, in a flexed position from the application of a flexion force F4 and in a default position to which the mechanism returns via a self-return elastic means or mechanical means 13 generating an extension force, wherein said elastic means 13 is coupled to any mobile link of the mechanism and to a fixed or reference position 10. In this sense, it can be appreciated how the elastic means 13 is coupled from a reference or fixed position 10 to the first link 21; however, those skilled in the art will appreciate that the link to which said elastic means 13 is coupled may vary without affecting the subject matter of the present invention.

Figure 2H:
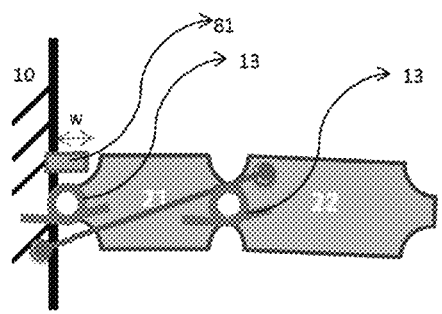
FIG. 2H shows a mechanism with two links, wherein said mechanism includes an elastic means defined by a spring coupled to the first joint, and wherein said mechanism further includes an adjustable restraint stop or projection for adjusting the default position of the mechanism when a flexion force is no longer applied.

FIG. 2H shows a segment of a mechanism in one embodiment of the present invention, wherein at least one self-return mechanical means 13, also called elastic means 13, is coupled, said mechanical means applying in this case an extension force at least in one of its vector components, thereby causing the self-return of the mechanism when an activation force is ceased to be applied, in this case the flexion force, or when said force has been defeated. A person skilled in the art will appreciate that the technique to generate the extension force for the self-return via the elastic means 13 to a default position may vary without affecting the subject matter of the present invention, with said elastic means being selected from the list of: elastic bands, springs or torsion springs of different types, compression springs of different types, extension springs of different types, flexion springs of different types, an elastic material, a shape memory material, etc. Furthermore, a person skilled in the art will appreciate that the spring may be coupled to the mechanism by using techniques known in the art, so that, once said spring is coupled, an extension force and/or a flexion force and/or combinations thereof may be generated, thereby causing the mechanical self-return of the mechanism to a default position or to any other desired position. Additionally, a person skilled in the art will appreciate that the mechanical properties of the spring may vary without affecting the subject matter of the present invention, including the elasticity module, material, thickness, methods and spinning direction (Z- or S-twist), dimensions, and/or geometrical shape. In this sense, as shown in the Figure, in one embodiment of the invention, the elastic means 13 is defined by an extension spring coupled to the joint, such that both of them are concentric and parallel, and one of the spring ends is fixedly coupled to a link 21 and the other of the spring ends is also fixedly coupled to the other link which in this case is the fixed reference 10. In one embodiment of the invention, the elastic means 13 is coupled between mobile links, as shown in the Figure. In one particular embodiment, at least two elastic means 13 are coupled per each finger prosthesis. Furthermore, a restraint projection 81 is shown, said restraint projection defining o restraining the mechanism movement to a desired position or to a default position when said mechanism is returning via the self-return mechanical means 13. Said restraint projection 81 including dimensions which the return movement restraint of said mechanism will rely upon, normally defined by distance w. Thus, in one embodiment of the invention, said restraint projection 81 is defined by a screw threaded at a certain height in at least one link (where the respective perforation and threading were made), such that the thread depth of the screw may be adjusted by rotating the screw in one direction or the other; distance w may also be adjusted, as well as the desired or default position to which the mechanism will return via the self-return means 13 and/or via an external force. In one particular embodiment, the restraint projection 81 is a threaded insert. Those skilled in the art will appreciate that the number of self-return elastic means 13 may vary without affecting the subject matter of the present invention. Furthermore, those skilled in the art will appreciate that the elastic means 13 may be located in the first lateral rotation, in the second lateral rotation and/or in any other joint.

Those skilled in the art will appreciate that the point of application within the mechanism of the self-return means 13 may vary without affecting the subject matter of the present invention.

Figure 3A:
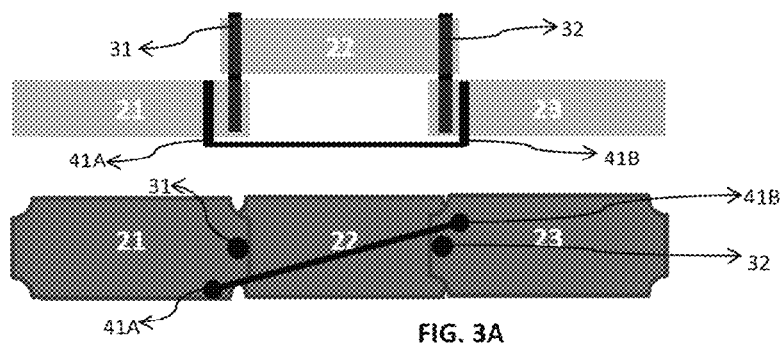
FIG. 3A shows a top side view of the same three-link kinematic chain of the present invention, depicting the way in which each joint crosses or is in direct contact with at least two links, and each rod end providing for pivoting only touches a corresponding link.

FIG. 3A shows an upper side view of a kinematic chain with three links 21, 22, and 23 according to one embodiment of the present invention, wherein said Figure shows a pivot rod 41 having rod ends 41A and 41B. The upper view of said Figure shows the manner in which each joint crosses or touches two links to provide the degree of freedom between said links; said Figure further shows the manner in which each pivot rod end only touches one link. Those skilled in the art will appreciate that the depth of the pivot and/or the joint within the respective link(s) may vary without affecting the subject matter of the present invention. In one embodiment of the invention, the pivot rod at least partially passes outside the links. In one particular embodiment, said links include a hollow design that allows for the pivot rod to at least partially pass inside the link(s). In one particular embodiment, the pivot rod passes outside and/or inside said links with or without touching them.

Figure 3B:
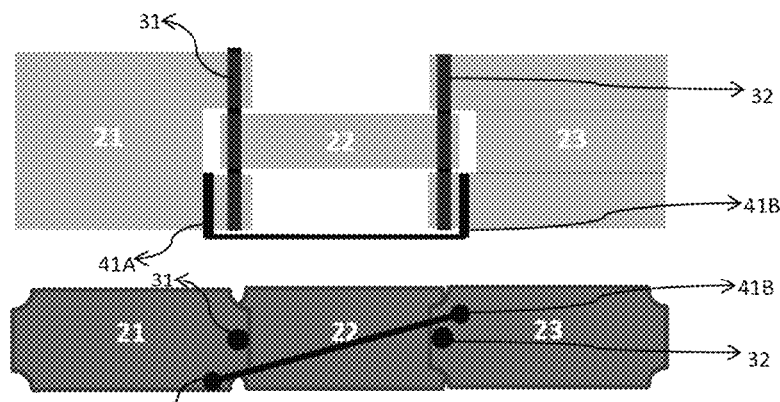
FIG. 3B shows a top side view of the same three-link kinematic chain of the present invention, wherein said links have a different configuration to connect with each other with respect to FIG. 3A, but maintaining the same pivoting.

FIG. 3B shows an upper side view of a kinematic chain similar to that in FIG. 3A, wherein the links have different shapes, but maintaining its articulated relationship. Thus, a person skilled in the art will appreciate that the shape of the links and the way in which they are coupled o connected with each other may vary without affecting the subject matter of the present invention.

Figure 3C:
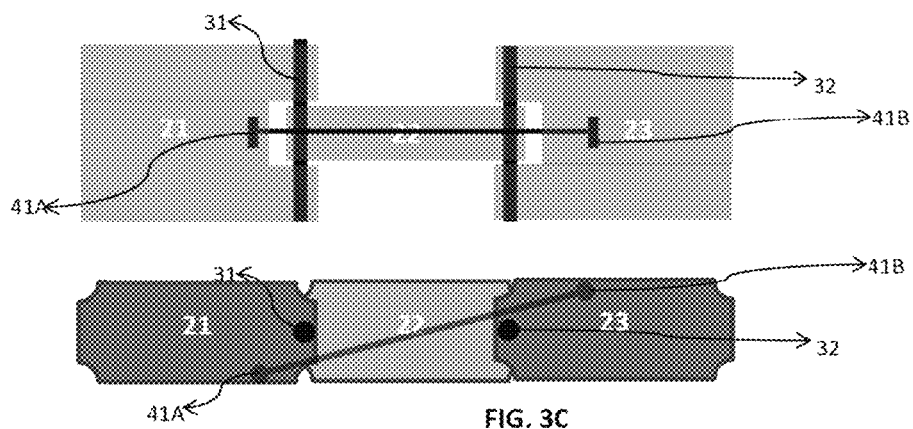
FIG. 3C shows the kinematic chain in FIG. 3B, wherein the pivot rod changes its location to internally cross a hollow link, but maintaining the same pivoting.

FIG. 3C shows an upper side view of the chain in the previous Figure, wherein the way in which the pivot rod is coupled to the links is different, i.e. instead of passing outside the links, said pivot rod passes inside the links, and the articulated relationship also takes place inside the link.

Figure 3D:
FIG. 3D shows a side view of the three-link kinematic chain of the present invention, wherein the pivot rod has changed in shape so as to avoid any physical obstacles, such as the dimensions and configuration of the links and/or joints.

FIG. 3D shows a side view of a chain with links 21-23 according to one embodiment of the present invention, wherein the pivot rod has an irregular shape. In this sense, in one embodiment of the invention, the rod is a rod having a curved portion in its distal ends. In one embodiment of the invention, the rod maintains a curved and/or irregular shape. In this sense, a person skilled in the art will appreciate that the shape of the rod may vary in any of its three dimensions without affecting the subject matter of the present invention.

The pivot rod being a solid elongated piece with a variable shape manufactured from a rigid material. In one particular embodiment, the pivot rod is manufactured with a resilient flexible material. Furthermore, in one embodiment of the invention, the way in which the pivot rod ends are coupled to the respective links is by means of a shaft or bolt with a bearing or similar device. Furthermore, in one embodiment of the invention, the pivot rod ends are defined by some crank-type laterally parallel cross bars providing the pivoting.

Figure 4A:
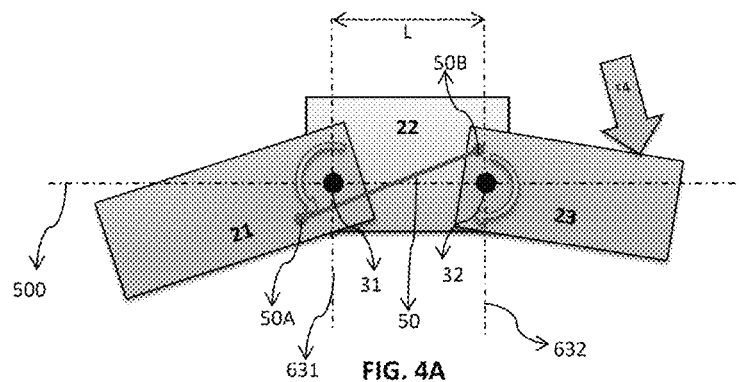
FIG. 4A shows a diagram of the kinematic chain of the present invention, with three links 21, 22, and 23, wherein the pivot rod is coupled for providing the pivoting of links 21 and 23 with respect to link 22. Furthermore, the rotation in an opposite direction of said links 21 and 23 with respect to link 22 can be observed.

FIG. 4A shows a three-link kinematic chain according to one embodiment of the present invention, wherein said Figure illustrates links 21, 22, and 23; joint 31 hingedly connecting links 21 and 22 with each other; and joint 32 hingedly connecting links 22 and 23 with each other, wherein joints 31 and 32 are separated by a distance L. Additionally, said Figure illustrates pivot rod 50, wherein one rod end 50A is hingedly coupled to link 21, and the other rod end 50B is coupled to link 23. Furthermore, taking link 22 as a reference, the behavior of links 21 and 23 when a force F4 is applied can be observed, wherein the rotations are in opposite directions, i.e. link 23 rotates clockwise, and link 21 rotates counterclockwise. Furthermore, distance L between joints 31 and 32 can be appreciated. Additionally, the pivot axis 500 defined as a straight line crossing the center of a joint with the center of another adjacent joint can be appreciated. As the mechanism moves, the pivot axis 500 of each arrangement of links also modifies its slope and displacement, wherein the pivot axis 500 is used to illustrate the location of the pivot rod ends, either in a quadrant and/or hemisphere with respect to said axis 500. A person skilled in the art will appreciate that the number of pivot axes 500 may vary according to the number of hinged links in the mechanism. Once the pivot axis 500 is defined by projecting a traversal line 631 and 632 to said axis on each joint at one point in time, a Cartesian plane is formed, thus defining a pivot plane for each joint.

Figure 4B:
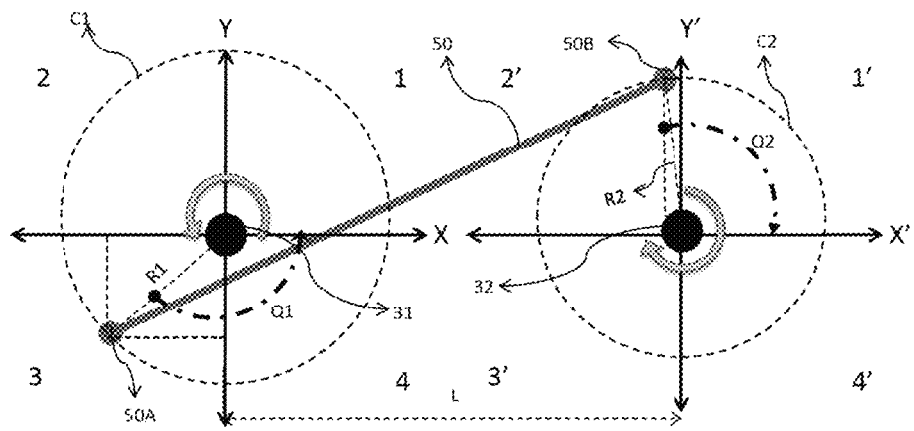
FIG. 4B shows the analysis of the pivoting movement in FIG. 4A by means of two Cartesian planes or pivot planes, with the pivot rod ends being placed in opposite hemispheres with respect to the horizontal axis or X axis, wherein the pivoting movements of links 21 and 23 with respect to its corresponding joints can be observed.

FIG. 4B shows an analysis of the movements of the parts comprising the chain in FIG. 4A, taking as a reference joints 31 and 32 on which the Cartesian planes are placed. Thus, said Figure further illustrates the separation distance L between the joints, the distance of arms R1 and R2 corresponding to the pivoting radius or separation distance between each pivot or pivot rod end 50A and 50B with its corresponding joint 31 and 32, respectively, and wherein it can be appreciated that said rod ends 50A and 50B are in opposite hemispheres and that they will move within said hemispheres from a reference position until they have at least partially move through angle Q1 and Q2, either in one direction to generate the flexion movement or in the other direction to generate the extension movement, depending on the activation force being applied. The way in which the links are located relative to each other is a reference position or at one point in time. Thus, when a force F4 is applied to link 23, said link starts to rotate and to trigger movement of link 21 in response of the pivot rod 50 and the articulated relationship maintained by links 21 and 23 with link 22. In this sense, a person skilled in the art will appreciate that if link 21 is taken as the fixed reference, when a force F4 is applied, a flexion movement will be triggered in the other links. Although the pivot rod end 50B is located at a separation distance R2 defining a circumference C1, it is important to mention the initial application angle of said rod end 50B on circumference C1 and its travel arc Q2 once a force F4 is applied. In this sense, the closer a pivot rod end is to the Y axis, i.e. an angle of about 90°, then its displacement component in X will be greater with respect to its displacement component in Y, and vice versa. That is, the displacement movement in X and in Y has a sinusoidal and a cosinusoidal behavior. Furthermore, this FIG. 4B illustrates, in addition to the opposite hemispheres, the quadrants in which each pivot rod end 50A and 50B are located at the beginning of the travel. Thus, in one embodiment of the invention, the first end 50A of pivot rod 50 is in quadrant 3 of its respective plane, and the second end 50B of pivot rod 50 is in quadrant 2' of its respective plane. In one particular embodiment, the first end 50A is in quadrant 3, and the second end 50B is in quadrant 1'. In one particular embodiment, the first end 50A is in quadrant 4, and the other end 50B is in quadrant 1'. In one particular embodiment, the first end 50A is in quadrant 4, and the other end 50B is in quadrant 2'. A person skilled in the art will appreciate that the location of the ends of the pivot rod changes according to the general movement of the mechanism; however, the locations illustrated herein are locations in a reference position, such as in an at least partially extended position, in a completely extended position until a physical restraint of the same mechanism is reached, in an at least partially flexed position, or in a completely flexed position until a physical limit of the mechanism is reached. In one embodiment of the invention, the physical limit of the mechanism may be adjusted by means of a limit adjuster or restraint projection 81 (not shown in this Figure) already explained.

Figure 4C:
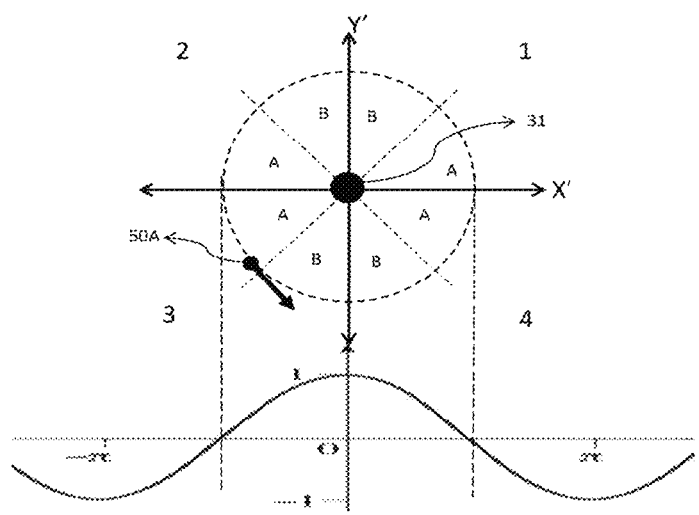
FIG. 4C shows a diagram of the change of velocity with a sinusoidal/cosinusoidal behavior of the pivot rod end when said pivot rod end rotates around the joint, and moving closer to or away from the horizontal and/or vertical axes.

FIG. 4C shows the behavior of pivot end 50A when displaced on the arc of an hemisphere from quadrant 3' to quadrant 4' of its respective joint 31, and wherein said figure further shows its graph of displacement in X, which has a cosinusoidal behavior that, in this case, is complemented with the cosinusoidal displacement of the other pivot end 50B (not shown in figures) to generate the resulting movement. Furthermore, said Figure shows a subdivision of the quadrants into angle regions, either close to X axis, for example the range of angle A, moving away or moving closer to said X axis, or close to Y axis, for example the range of angle B, moving closer or moving away, depending on the direction of the rotation. Thus, it can be observed how the pivot end 50A starts its stroke along the arc formed by quadrants 3 and 4 located specifically in the region of angles A moving away from the X axis. In this sense, with regard to the mechanism of the present invention and FIG. 4B and the rotation direction of said mechanism, when the first and/or second pivot rod end is within the range of angles B moving closer to the Y axis, then the rotation of the farthest link relative to said pivot rod is faster and its velocity increases as compared with the rotation velocity of said link if it were, for example, in region A. A person skilled in the art will appreciate that the division of the quadrants into regions applies to all the quadrants of the Cartesian plane and to both pivot rod ends, either separately or in combinations thereof. Furthermore, a person skilled in the art will appreciate that the rotation velocities of the second link 23 at different times with respect to link 22 applies to both directions of the rotation by applying an flexion or extension force of activation. Additionally, a person skilled in the art will appreciate that the number of links, pivot rods and its location may vary without affecting the subject matter of the invention, wherein the relationship of distances, radii, rotation angles, etc., may be the same or different from some links with respect to other links in the same mechanism. In one particular embodiment, each angle region A and/or B has an angle range from 0-90°. In this sense, a person skilled in the art will appreciate that the manner in which the angle regions are termed or classified may vary without affecting the subject matter of the present invention.

In this sense, it will be apparent to a person skilled in the art that, from the subject matter disclosed herein, it is possible to design different prosthesis with pivoting combinations in different quadrants, such as 3-2', 3-1', etc. That is, in quadrants crossing, or being opposite with respect to, an axis, in this case the X axis or horizontal axis. Additionally, a person skilled in the art will appreciate that each pivot does not necessarily rotate completely around its respective joint, since, depending on the leverages and the length of the pivot rod, a mechanical restraint will be reached, such that said restraint will indicate the end of the pivot rotation (and thus the link where said pivot is located) with respect to the joint (or with respect to the previous adjacent link). Therefore, the movement of each pivot ranges from 0° to a maximum of 180° to be able to achieve the desired rotation in a prosthesis, otherwise, if the pivot continuous rotating, the movement will change its direction by exhibiting a sinusoidal behavior. Thus, the component in X moving in a pivot rod end will be substantially reflected in the other pivot rod end X, since this is a rigid rod that is pushed or pulled, and the same applies to the component in Y. Therefore, the length of the rod and the leverages have a direct relationship with the resulting movement, velocity, times and restraints of the prosthesis.

Figure 4D:
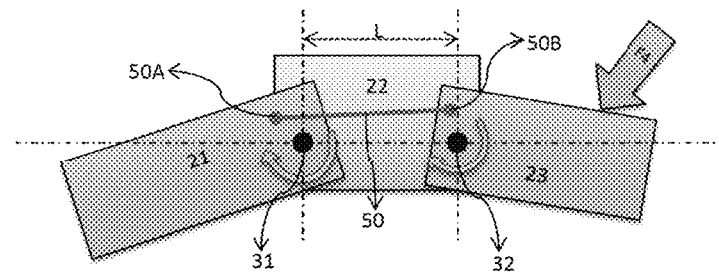
FIG. 4D shows a diagram of a kinematic chain with three links 21, 22, and 23 in one embodiment of the present invention, wherein the pivot rod is coupled for providing the pivoting of links 21 and 23 with respect to link 22. Furthermore, the rotation in the same direction of said links 21 and 23 with respect to link 22 can be observed.

FIG. 4D shows a kinematic chain according to one embodiment of the invention, with links 21, 22, and 23, wherein the pivot rod ends 50A and 50B of pivot rod 50 are located in the same plane hemispheres relative to joints 31 and 32, in an initial movement or reference position.

Figure 4E:
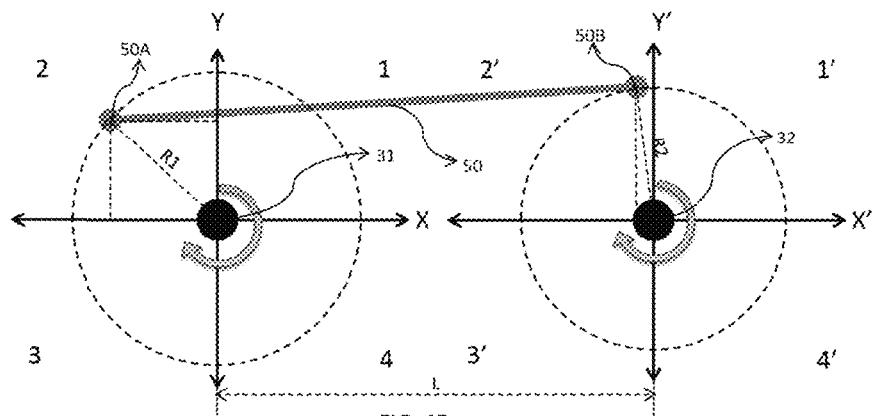
FIG. 4E shows the analysis of the pivoting movement in FIG. 4D by means of two Cartesian planes or pivoting planes, with the pivot rod ends being placed in the same hemispheres with respect to the horizontal axis or X axis, wherein the pivoting movements of links 21 and 23 with respect to its corresponding joints in the same direction of rotation can be observed.

FIG. 4E shows the analysis of the movement of the chain in FIG. 4D, with pivot rod ends 50A and 50B being located in the same hemisphere (either upper or lower) with respect to the horizontal or X axis, wherein it can be appreciated that the rotation direction of link 21 and 23 is the same with respect to link 22, thereby resulting in a link performing a flexion movement, and in the other link performing an extension movement, both relative to link 22. Furthermore, it can be appreciated that the length of the pivot rod 50 is greater than the separation distance between the joints L. A person skilled in the art will appreciate that the pivot rod ends located in the same hemispheres could be upper and/or lower hemispheres without affecting the subject matter of the present invention. Additionally, a person skilled in the art will appreciate that the difference between the length of the pivot rod and the separation distance between the joints L may vary without affecting the subject matter of the present invention.

Thus, in one embodiment of the invention, a finger prosthesis is provided from a mechanism of the present invention, said mechanism having at least four links connected by a joint providing at least one degree of freedom to a lateral rotation, wherein said first link is considered as fixed by being coupled to the biological part of a patient or user. Furthermore, the counting of joints, links and/or pivot joints starts from the reference or fixed link. The prosthesis including at least three joints and at least two pivot rods whose pivot rod ends are located in opposite hemispheres from a reference or initial flexion and/or extension movement position. In one embodiment of the invention, the separation distance of the first joint from the second joint is less than the separation distance of the second joint from the third joint. In one embodiment of the invention, the length of the first pivot rod is less than the distance of the second pivot bar. In one embodiment of the invention, the length of the second pivot rod is greater than the separation distance between the second joint and the third joint in a range from 1-20%. In one embodiment of the invention, the length of the first pivot rod is less than the separation distance between the first joint and the second joint in a range from 1-20%. In one embodiment of the invention, the separation distance between the first pivot rod end and its corresponding joint is greater than the separation distance of the second pivot rod end and its corresponding joint. In one embodiment of the invention, the separation distance between the first pivot rod end and its corresponding joint is less than the separation distance of the second pivot rod end and its corresponding joint. In one embodiment of the invention, the separation distance of the rod ends from its corresponding joint is substantially the same. In one embodiment of the invention, in an initial and/or reference position of the prosthesis mechanism to start the flexion movement, the first end of the first and/or the second pivot rod is located in region A moving away from the X axis. In one particular embodiment, in an initial and/or reference position of the prosthesis mechanism to start the flexion movement, the first end of the first and/or the second pivot rod is located in region B moving closer to the Y axis. Furthermore, a person skilled in the art will appreciate that these distances and lengths may apply to rod ends in the same and/or opposite hemispheres.

Figure 5A:
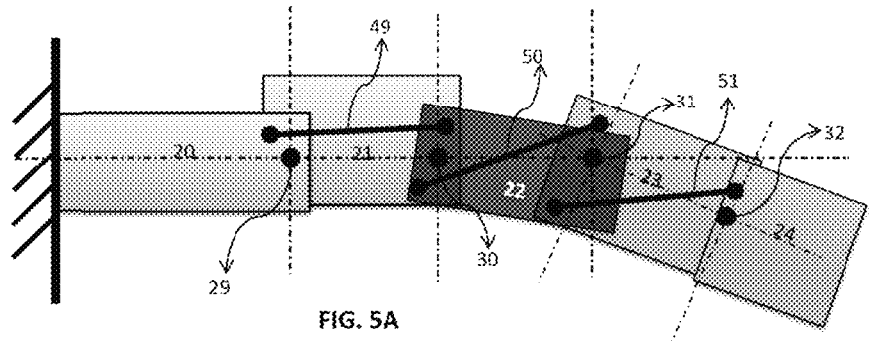
FIG. 5A shows a mechanism comprised by links 20, 21, 22, 23, and 24, wherein the pivot rods are coupled to non-adjacent links, and wherein the first pivot rod providing the pivoting of links 20 and 22 with respect to link 21 is coupled to the same hemispheres, and the other pivot rods are coupled to opposite hemispheres.

FIG. 5A shows a mechanism according to one embodiment of the present invention in an initial movement and/or reference position, said mechanism including five links 20, 21, 22, 23, and 24 connected in sequence by joints 29, 30, 31, and 32, wherein link 20 is a fixed link and, for purposes of illustration, link 22 includes a color that allows to see the pivot rod 50 located behind or inside said link (transparency). Additionally, said mechanism including three pivot rods 49, 50, and 51, wherein the rod ends 49 are located in the same hemispheres, in this case in the upper hemispheres, and the pivot rod ends 50 and 51 are located in opposite hemispheres, in this case in the lower hemisphere firstly and in the upper hemisphere secondly. Furthermore, the pivot planes for each joint can be observed, which are useful for analyzing the pivot movement of some links relative to other links.

Figure 5B:
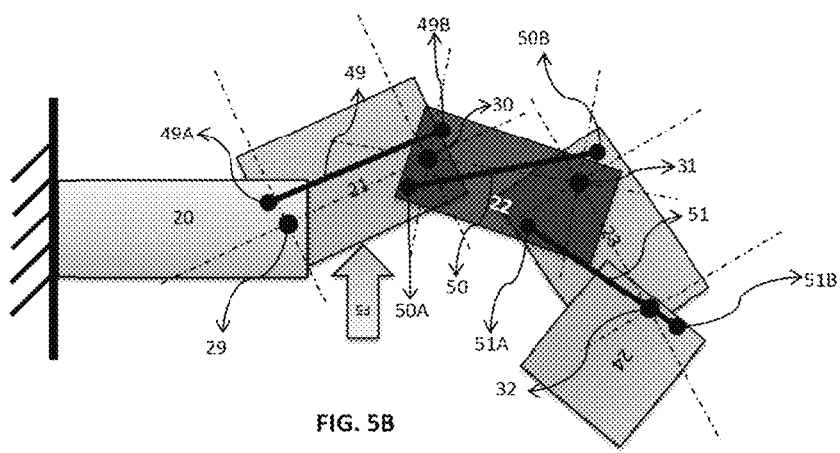
FIG. 5B shows the mechanism in FIG. 5A, wherein a force F5 is applied in this configuration for providing an extension movement in link 21.

FIG. 5B shows the behavior of the mechanism in FIG. 5A when an extension force F5 is applied, thereby generating an extension movement only in link 21. Thus, due to the location (the same hemispheres) of the rod ends 49A and 49B, the pivot rod 49 will push and exert a flexion movement on link 22, thereby generating a triggered flexion movement in links 22, 23, and 24 relative to link 21. In one embodiment of the invention, link 20 is defined by a link the shape and material of which fit the shape of the biological forearm of a user or patient. In one embodiment of the invention, link 20 corresponds to the biological forearm of a user or patient, joint 29 corresponds to a joint and/or a user's biological wrist providing at least one lateral degree of freedom, at least partially; link 21 corresponds to a link the shape of which allows to accommodate the palm or a portion of the biological cut off palm of a user. In one embodiment of the invention, the first end 49A of the pivot rod 49 is attached to the forearm and/or link 20 via a mechanical means known in the art. In one particular embodiment, the rod end 49A is coupled to the forearm by means of a wristlet or belt including at least a projection having a joint inlet through a bolt allowing for at least one lateral rotation. In one embodiment of the invention, it is included one projection for each finger prosthesis with a joint inlet through a bolt allowing at least one lateral rotation.

In one embodiment of the invention, a finger prosthesis is provided from a mechanism with at least two hinged links having pivot rods hingedly coupled to non-adjacent links, wherein the pivot ends of at least one pivot rod are located in the same hemispheres with respect to its corresponding joint, and the pivot ends of at least another pivot rod are located in opposite hemispheres with respect to its corresponding joint, in an initial or reference position of the prosthesis.

Figure 6A:
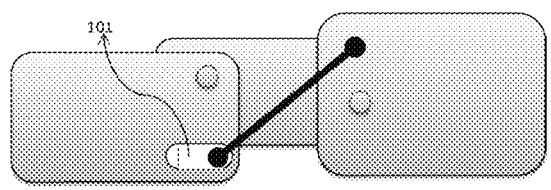
FIG. 6A shows a chain with three hinged links and a pivot rod in adjacent links, in opposite hemispheres, wherein the articular relationship of one of the pivot rod ends further provides for displacement.

FIG. 6A shows a kinematic chain of the present invention, wherein different types of articulated relationship can be observed, either in the joints and/or in the coupling of the pivot rod ends. Thus, in addition to the joints providing a lateral rotation, said Figure also shows the joint with lateral rotation and slider 101, which allows not only a lateral rotation, but also an at least partially horizontal displacement. A person skilled in the art will appreciate that the horizontal displacement may vary to be a vertical or lateral displacement or a combination thereof without affecting the subject matter of the present invention.

Figure 6B:
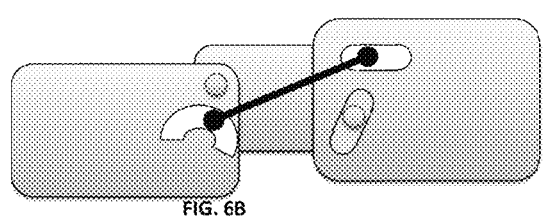
FIG. 6B shows a chain with three hinged links and a pivot rod in adjacent links, in opposite hemispheres, wherein the joints and the articular relationship of the pivot rod ends, in addition to providing at least one angular degree of freedom (lateral rotation), further provide for partial displacement degree of freedom at least on the horizontal axis or X axis and/or on the vertical axis or Y axis.

FIG. 6B shows a kinematic chain of the present invention, wherein combinations of joints with regular and irregular displacements are used, either in the joints and/or in the pivot providing for the pivot rod ends.

Figure 6C:
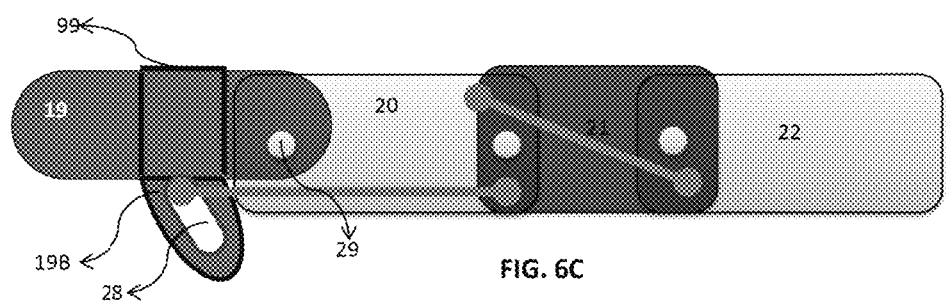
FIG. 6C shows a chain according to one embodiment of the present invention, depicting four links with the first link being fixed with respect to the other links, and two pivot rods applied to non-adjacent links, with the first rod being located in the same hemispheres and the second rod being located in opposite hemispheres, and wherein the first end of the first pivot rod includes an articulated relationship of lateral rotation and also displacement in both axes of the plane.

FIG. 6C shows an example of the operation of a mechanism including a slider displacement joint 28 according to one embodiment of the invention, wherein said figure further shows the pivot rod coupled to the same or opposite hemispheres. In this sense, link 19, which can be considered to be a fixed link, includes a link projection 19B where the slider joint 28 is located. In one embodiment of the invention, the link projection 19B is integral with the link 19. In one embodiment of the invention, the link projection is a separate piece. In one particular embodiment, the link projection 19B is a separate piece coupled to link 19 by means of a belt or wristlet 99. Furthermore, in one embodiment of the invention, link 19 corresponds to the biological forearm of a user, wherein the link projection 19B is coupled to said forearm. In one embodiment of the invention, link 20 is a link the shape of which allows for accommodation of the biological palm with or without biological fingers of a user. In one embodiment of the invention, joint 29 corresponds to the biological joint of a user, i.e. the wrist, and/or a mechanical joint already explained herein.

Figure 6D:
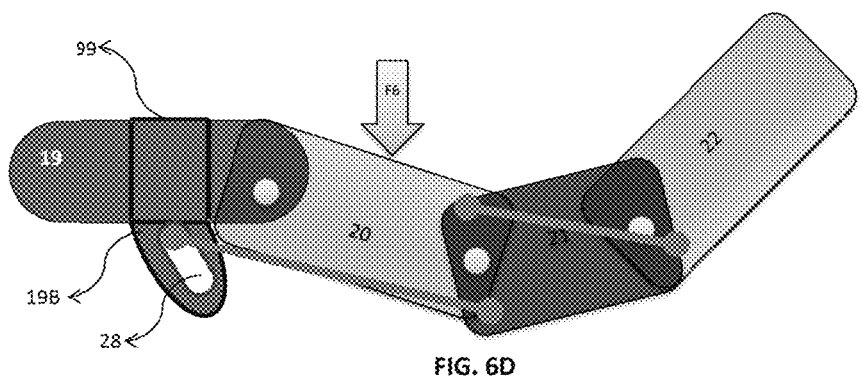
FIG. 6D shows the chain in FIG. 6C, wherein a force F6 has been applied to the second link so as to generate an extension movement in said link, and a triggered flexion movement in the subsequent links.

FIG. 6D shows the behavior of the mechanism in FIG. 6C, wherein a force F6 is applied, thereby generating a flexion movement (or extension movement according to the reference) in one of the links, such that said movement is spread along the other links as already explained.

Figure 6E:
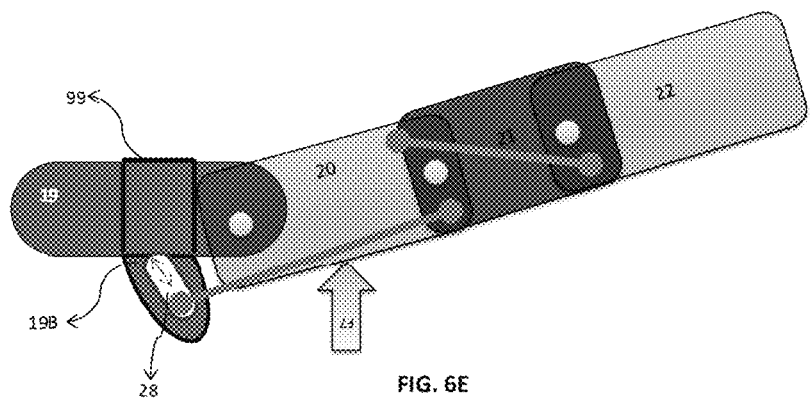
FIG. 6E shows the chain in FIG. 6C, wherein a force F7 is applied in an opposite direction with respect to force F6 in FIG. 6D, wherein the displacement degree of freedom of the first rod end of the first pivot rod causes the pivoting to be cancelled.

FIG. 6E shows the same mechanism as in FIG. 6C, wherein now a force F7 is applied, thereby generating a movement that is opposite to the force F6 applied to the mechanism shown in FIG. 6D, and wherein it can be appreciated that such displacement allowed by the displacing joint 28 prevents force F7 from generating a spread movement in the flexion or extension links, since it at least partially nullifies the pivoting.

Figure 7A:
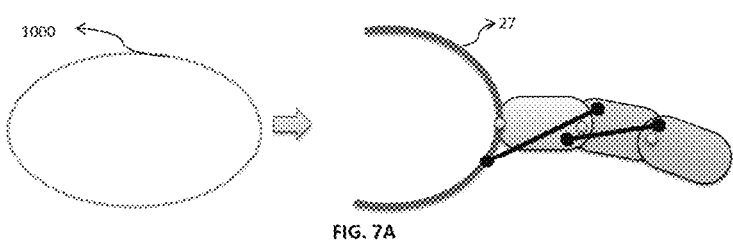
FIG. 7A shows a side view of a first momentum of assembly of the prosthesis into a biological part.

FIG. 7A shows a side view of a prosthesis coupling to a biological limb 1000 of a user or patient according to one embodiment of the present invention, wherein link 27 allows to at least partially accommodate a biological limb of a user or patient. Said link 27 is manufactured from a heat moldable material, such as a plastic or the like. A person skilled in the art will appreciate that link 27 may change in shape or dimensions according to the limb or residual limb 1000 to be accommodated without affecting the subject matter of the present invention. In one embodiment of the invention, link 27 consists of at least one curved strip, wherein the curvature of the curved strip substantially corresponds to the shape of the limb or residual limb to be accommodated.

Figure 7B:
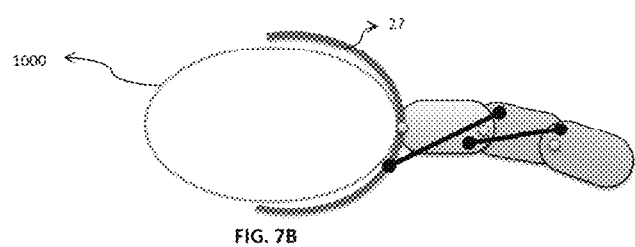
FIG. 7B shows a side view of a biological part accommodated by the prosthesis, said prosthesis housing being moldable.

FIG. 7B shows the example provided in FIG. 7A, wherein the biological limb has been introduced into the link 27. Said link 27 has been manufactured maintaining substantially the same design as that of the biological limb or residual limb to be accommodated.

Figure 7C:
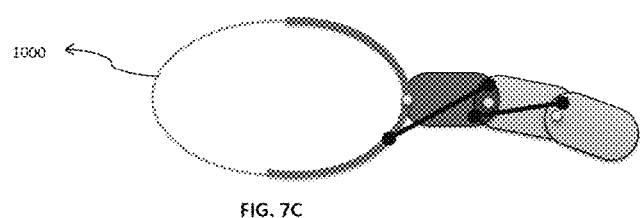
FIG. 7C shows a side view of a prosthesis accommodating a biological part, wherein said prosthesis has been molded so as to fit the specific shape of the biological part.

FIG. 7C shows the example provided in the previous figure, wherein heat has been applied to allow for heat molding of link 27 to particularly fit the physiological characteristics of the limb or residual limb to be accommodated.

Figure 8:
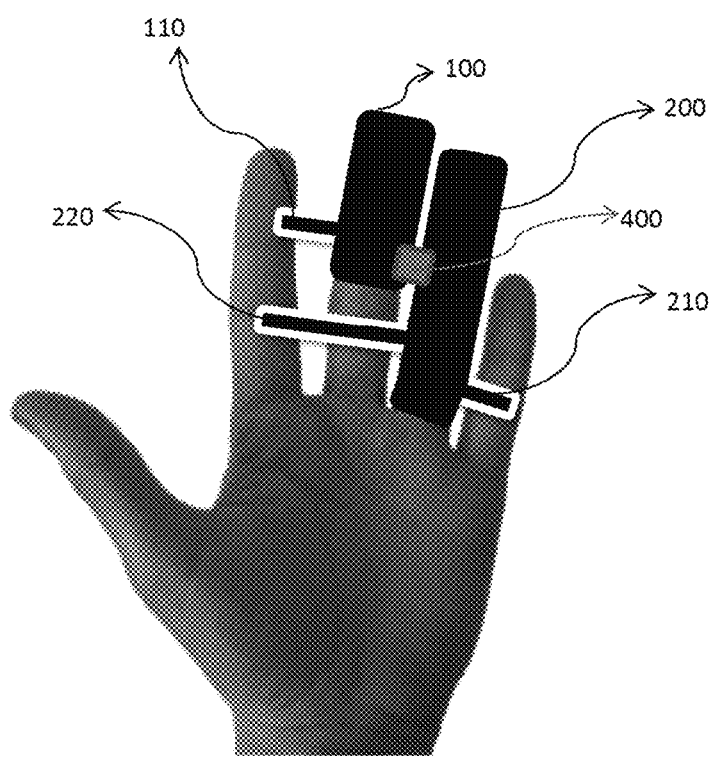
FIG. 8 shows a lower view of a hand with the third and fourth fingers cut off, wherein prostheses have been applied and arranged such that at least a lever or trigger pushed by the biological part(s) activate said prostheses.

FIG. 8 shows a lower view of a hand whose third and fourth fingers are missing all phalanges, and wherein prosthesis have been applied according to one embodiment of the present invention. In this case, the third finger is missing a distal phalange and is also partially missing a middle phalange, and the fourth finger is missing all of its phalanges. Furthermore, in one embodiment of the invention, a connection element 400 is shown, which connects two adjacent finger prostheses to provide support and to ensure an even movement. In one particular embodiment, the connection element 400 separately connects two adjacent finger prostheses.

Thus, said figure shows how prostheses 100 and 200 are coupled to the third and fourth fingers, respectively. In this sense, it can be observed that each prosthesis includes at least one trigger or flexion activation means defined by an extension laterally extending to a point of said prosthesis, either in one direction or in the other. In this sense, prosthesis 200 includes a trigger 210, which is activated by the fifth finger at a height between the middle and the proximal phalange of said fifth finger. Furthermore, it can be observed how the prosthesis for the fourth finger 200 includes a second trigger to be activated by the second biological finger and/or by the stump of the third finger. Additionally, the finger prosthesis includes a trigger 110 activated by the second biological finger. A person skilled in the art will appreciate that the number of triggers for each prosthesis, its direction, its location, and its length to be activated by more than one biological finger or stump may vary without affecting the subject matter of the present invention. Furthermore, a person skilled in the art will appreciate that the technique according to which triggers are coupled to the prosthesis is already known in the art and that it may vary without affecting the present invention, and that said trigger may be a trigger coupled by using a screw-nut relationship, by thermo-fusion or welded with or without a filler material, or by a simple male-female assembly relationship, etc. In this sense, in one embodiment of the invention, the simple male-female assembly relationship includes magnetic means for keeping in place the assembly elements. A person skilled in the art will appreciate that the triggers may be coupled to be activated by flexion and/or by extension.

In one embodiment of the invention, triggers 110, 220, and 210 are parallel triggers. In one embodiment of the invention, triggers 110, 220, and 210 are substantially parallel triggers.

In one embodiment of the invention, said trigger is coupled to a bearing inside the prosthesis. In one particular embodiment, said bearing includes a self-alignment mechanism to compensate for misalignment in the biological fingers and/or stumps, thereby enabling triggers to be misaligned.

In one embodiment of the invention, the trigger length is such that it encompasses the width of more than one biological finger or stump. Furthermore, in one embodiment of the invention, the trigger is irregular in shape so as to fit the biological shape of the fingers and/or stumps that will activate said trigger. In one embodiment of the invention, said trigger projects laterally plus an inclination range to fit the biological shape of the fingers and/or stumps that will activate said trigger. In one particular embodiment, said inclination ranges from +−15° in both planes defined by the lateral axis. In another particular embodiment, the trigger length ranges from 1.5 to 8 cm, thereby being able to be activated by one, two or even three biological fingers and/or stumps. A person skilled in the art will appreciate that the trigger inclination may be given by the own shape of the trigger, which would not be straight, or by an inclination in the receptacle receiving a straight trigger.

In one embodiment of the invention, each trigger includes padded, antiskid, and/or hypoallergenic material on the trigger surface.

A person skilled in the art will appreciate that the number of links for each mechanism and the manner of obtaining the degrees of freedom of the joints described herein may vary without affecting the subject matter of the present invention, wherein a shaft or simple or complex spindle, a bearing coupled to a cylinder, a hinge, or more complex mechanical arrangements already known in the art which provide the degrees of freedom to each hinged pivot or joint may be included. Including slider joints or additional degrees of freedom, wherein said additional degrees of freedom may or may not be displacement degrees of freedom.

Furthermore, a person skilled in the art will appreciate that the number of finger prosthesis mechanisms for each hand may vary without affecting the subject matter of the present invention, wherein said prosthesis mechanisms are coupled in parallel, either rigidly, semi-rigidly and/or independently connected or not with each other.

In one embodiment of the invention, each joint is defined by at least one circular orifice having a diameter D concentrically crossing at least two corresponding links, and wherein a cylindrical rod, shaft or bolt having a diameter substantially equal to or less than D is introduced through said at least one orifice, such that, when it is introduced, it allows for said links to have an articulated relationship, thereby providing for a lateral rotation with each other. In one embodiment of the invention, one bearing is coupled to said at least one orifice between the rod and each link, such that said bearing provides strength wear resistance and reduces friction. In one particular embodiment, said at least one orifice has a slider-type elongated shape, such that the cylindrical rod may rotate and displace back and forth along said elongated shape according to the mechanism movement.

In one embodiment of the invention, at least one link joint, in addition to providing a lateral rotation, also provides an at least partially longitudinal rotation and/or an upper rotation.

Furthermore, a method for coupling the prosthesis of at least one finger to the biological hand is provided. In this sense, the finger prosthesis includes, in one of its ends that would be in contact with said hand, said end being fixed relative to the other links, curved strips coupled to said end, such that the strip curvature at least partially traps the hand. Additionally, in one embodiment of the invention, said curved strips are manufactured from a flexible material to be coupled to the hand or palm in a more tightly manner. In one particular embodiment, the curved strips are manufactured from a heat moldable material.

In one embodiment of the invention, each trigger is manufactured from a material different from the material of the links. In one particular embodiment, the triggers are manufactured from a metal known in the art, such as any aluminum alloy, steel, bronze, copper, etc.

In one embodiment of the invention, the trigger is coupled to the link by two receptacles in the link, wherein the trigger shape fits both receptacles at the same time. In one particular embodiment, the trigger or trigger arrangement has an "L" and/or inverted "T" shape which is separately coupled to the corresponding link by at least two nails, screws, bolts and/or magnetic bolt arrangements.

A person skilled in the art will appreciate that the curved strips may vary in its dimensions without affecting the subject matter of the present invention, wherein some of the strips may be longer than the others and/or some of the strips may be wider than the others. Furthermore, a person skilled in the art will appreciate that some of the strips may be different from or the same as the other strips.

Additionally, a person skilled in the art will appreciate that the shape of the links and the technique used to fit said shape to the different biological shapes of the body may vary without affecting the subject matter of the present invention.

Furthermore, a person skilled in the art will appreciate that the number of strips used to secure a prosthesis to the corresponding biological part may vary without affecting the subject matter of the present invention.

Thus, a mechanical prosthesis of at least one finger is claimed, wherein said prosthesis includes a default position, said prosthesis comprised by: a mechanism with at least three consecutive links numbered from the link closest to the biological part and hinged by a joint between links, said joint providing at least one degree of freedom of a link relative to another link, wherein each joint has as a reference a particular pivot plane comprised by a horizontal axis defined by a first straight line connecting the joint with a second adjacent joint and a vertical axis defined by a second straight line transversal to the first straight line and crossing the center of the joint; a pivot rod coupled to every two non-adjacent links of the mechanism, such that a rod end is coupled around a joint of one non-adjacent link and the other rod end is coupled around a joint of the other non-adjacent link, wherein the coupling of each rod end to the corresponding link is performed by means of at least one articulated relationship of rotation parallel to the joint of the mechanism; at least one elastic mechanical arrangement coupled to the prosthesis from a fixed reference for providing the prosthesis with a constant strength; wherein, in the default position, the first end of each rod is located, with respect to the joint to which said end is coupled around, in an hemisphere relative to the horizontal axis, and the second end of said rod is located, with respect to the joint to which said end is coupled around, in a hemisphere opposite to the hemisphere where the first rod end is located; and wherein, the prosthesis default position is at least partially modified by a force opposite to the force of the elastic mechanical arrangement applied by at least one trigger coupled to at least one link, wherein said trigger is defined by an elongated piece or projection protruding outwardly from the prosthesis and being at least partially parallel to the rotation axes of the joints of the mechanism.

Additionally, a mechanical prosthesis of at least one finger is claimed, said prosthesis including a default position, said prosthesis comprised by: a mechanism with at least four consecutive links numbered from the link closest to the biological part and hinged by an joint between links, said joint providing at least one degree of freedom of a link relative to another link; wherein each joint has as a reference a particular pivot plane comprised by a horizontal axis defined by a first straight line connecting the joint with a second adjacent joint and a vertical axis defined by a second straight line transversal to the first straight line and crossing the center of the joint; a pivot rod coupled to every two non-adjacent links of the mechanism, such that a rod end is coupled around a joint of one non-adjacent link and the other rod end is coupled around a joint of the other non-adjacent link, wherein the coupling of each rod end to the corresponding link is performed by means of at least one articulated relationship of rotation parallel to the joint of the mechanism; wherein, in the default position and from the second pivot rod, the first end of each rod is located, with respect to the joint to which said end is coupled around, in an hemisphere relative to the horizontal axis, and the second end of each rod is located, with respect to the joint to which said end is coupled around, in a hemisphere opposite to the hemisphere where the first rod end is located; and wherein, in the default position and for the first pivot rod, the first rod end is located, with respect to the joint to which said end is coupled around, in a hemisphere relative to the horizontal axis, and the second rod end is located, with respect to the joint to which said end is coupled around, in the same hemisphere as the first rod end.

The foregoing description of the various embodiments has been presented only for purposes of illustration and description. It is not intended to be exhaustive or to limit the invention to the precise forms disclosed. Therefore, many modifications and variations will become apparent to those skilled in the art. Moreover, the foregoing disclosure is not intended to limit the present invention.

The invention claimed is:

1. A mechanical prosthesis for at least one finger of a user, wherein said prosthesis comprises a default position, said prosthesis comprising:
   a mechanism with at least three consecutive links numbered from a link closest to a biological part and hinged by a joint between the links that provides at least one degree of freedom of a link relative to an adjacent link;
   at least one elastic mechanical arrangement that is coupled on one end to a link and on the other end to an adjacent link, wherein the arrangement is coupled to maintain the mechanism at least partially extended to define the default position;
   a pivot rod coupled between each two non-adjacent links of the mechanism in such a way that a first end of each pivot rod is coupled to a distal end of a first link around the joint between the links where it is pivoting and a second end of each pivot rod is coupled to a proximal end of a next non-adjacent link around the joint between the links where it is pivoting, wherein the coupling of each end of the pivot rod with a corresponding link is made through an articulated rotational relationship parallel to the joint between the links of the mechanism, and wherein each joint between the links where at least one end of the pivot rod is coupled, comprises as a reference a particular pivot plane comprising a horizontal axis defined by a first straight line connecting two joints between the links where the pivot rod is coupled, and a vertical axis defined by a second straight line transversal to the first straight line and crossing through the center of the joint; and
   at least one trigger coupled to any part of a surface of at least one link, wherein the trigger is defined by an elongated projection that rigidly protrudes outwardly from the prosthesis and partially parallel to a rotation axes of the joints between;

wherein in the default position, the first end of each pivot rod is in a hemisphere relative to the horizontal axis of the pivot plane of the joint to which is coupled, and the second end of each pivot rod is located in an opposite hemisphere respective to the hemisphere of the pivot plane of the joint to which is coupled;

wherein a number of links and a number and length of the at least one trigger is defined by a residual biological configuration of the user; and wherein each link comprises at least one receptacle around the surface, wherein each receptacle separably receives the at least one trigger.

2. The prosthesis according to claim 1, wherein the elastic arrangement is at least one of a torsion spring, an extension spring, a compression spring or an elastic band.

3. The prosthesis according to claim 1, wherein said at least one degree of freedom of a link relative to an adjacent link is an angular degree of freedom corresponding to a lateral rotation.

4. The prosthesis according to claim 1, wherein the first end of each pivot rod is in an upper hemisphere relative to the horizontal axis.

5. The prosthesis according to claim 1, wherein the second end of each pivot rod is in a lower hemisphere relative to the horizontal axis.

6. The prosthesis according to claim 1, wherein the at least one trigger is separately coupled to a link.

7. The prosthesis according to claim 1, wherein the length of the at least one trigger ranges from 1.5 to 8 cm.

8. The prosthesis according to claim 1, wherein at least one trigger is covered by at least one of padding or an antiskid layer.

9. The prosthesis according to claim 1, wherein the surface of at least one link comprises on a distal end, a restraint projection defined by a screw that modifies the link height when said screw is rotated in one direction or another.

10. The prosthesis according to claim 1, wherein the link closest to the biological part further comprises a mechanical coupling that couples with a cut off finger with or without a stump.

11. The prosthesis according to claim 10, wherein said mechanical coupling comprises curved strips made of moldable material.

12. The prosthesis according to claim 10, wherein the mechanical coupling further comprises a cavity in said link closest to the biological part, wherein a dimension of said cavity corresponds to a dimension of the biological part.

13. The prosthesis according to claim 1, wherein the pivot rod comprises a straight shape.

14. The prosthesis according to claim 1, wherein a shape of the pivot rod comprises at least one curve.

15. The prosthesis according to claim 1, wherein at least one pivot rod end is coupled either to the proximal end of a link or distal end of a link by means of the articulated rotational relationship and a partial displacement.

16. The prosthesis according to claim 1, wherein each joint or articulated rotational relationship further comprises a bearing comprising a self-alignment mechanism to compensate for misalignments.

17. The prosthesis according to claim 1, wherein the prosthesis is coupled to at least one other prosthesis by means of a connection element.

18. The prosthesis according to claim 17, wherein each connection element separately connects two adjacent prosthesis.

* * * * *